United States Patent [19]

Bean

[11] 4,132,782

[45] Jan. 2, 1979

[54] METHOD FOR SUPPRESSING HERPES SIMPLEX VIRUS

[76] Inventor: Samuel Bean, 22170 Marlowe, Oak Park, Mich. 48237

[21] Appl. No.: 798,585

[22] Filed: May 19, 1977

[51] Int. Cl.$^2$ ............................................. A61K 35/78
[52] U.S. Cl. ................................................... 424/195
[58] Field of Search ......................................... 424/195

[56] References Cited

U.S. PATENT DOCUMENTS 1,749,812  3/1930  Grube .................................. 424/195

OTHER PUBLICATIONS

Chemical Abstracts vol. 42:2020e (1948) & vol. 48:7844a (1954).

Potters, Cyclopaedia of Botanical Drugs & Preparations published by Potter & Clarke, Ltd. London, E. (1950) p. 238.

The Dispensatory of the U.S.A., 24th Ed. (1947) published by J. B. Lippincott Co., Phila, Pa. p. 1604.

*Primary Examiner*—Donald B. Moyer
*Attorney, Agent, or Firm*—Basile and Weintraub

[57] ABSTRACT

A method of treating herpes simplex by topical administration of the extract of mountain ash berries.

6 Claims, No Drawings

METHOD FOR SUPPRESSING HERPES SIMPLEX VIRUS

BACKGROUND OF THE INVENTION

1. Field of the Invention

This invention relates to a method of suppressing herpes simplex virus. More specifically, this invention relates to a method of suppressing herpes simplex virus by a topical administration of a solution of a mountain ash berry extract.

2. Description of the Prior Art

One of the simplest forms of treatment of herpes simplex virus consists of sponging with water, as hot as tolerable, followed by the local application of spirits of camphor, alcohol or equal parts of a tincture of benzoin, alcohol and glycerine. More recently, the use of idoxuridine has been advocated for this treatment. More recently, U.S. Pat. No. 3,818,103 teaches the use of sulfonoacetic acid or its salts as a means of combating the herpes simplex virus. U.S. Pat. No. 3,812,248 teaches the use of certain copolymers of divinyl ether and maleic anhydride to suppress the herpes virus. The embodiment of the instant invention afford a new means of suppressing the herpes simples virus.

SUMMARY OF THE INVENTION

In the method of suppressing the herpes simplex virus, an alcohol solution of the extract of mountain ash berries is applied topically to the site of the herpes eruption.

DESCRIPTION OF THE PREFERRED EMBODIMENT

In accordance with the invention, an extract of mountain ash berries, also known as Sorbus aucoparia fruit, is applied topically to the site of the herpes simplex virus eruption several times daily until relief from the lesions is obtained. In the preferred embodiment of the invention, an isopropanol solution of the extract of the mountain ash berries is applied topically to the site of the lesions. Although a solution containing from about 0.1 to about 20 percent by weight of the extract may be employed, a preferred concentration ranges from about 1 to about 5 weight percent of the extract.

The extract of the mountain ash berries is obtained by crushing a quantity of berries, adding a volume, of from 1 to 5 times the volume of berries, of 70 to 95 percent by volume isopropyl alcohol to the berries, and allowing the extraction to occur. This extraction is conducted by allowing the mixture of berries and alcohol to age at temperatures ranging from 20° C. to about 100° C. for a period of from about ten days to forty-five days. The upper range can be utilized providing that suitable means are available to condense the vaporized alcohol and return it to the extraction vessel. The solution is then filtered off from the berries by any means well known to those skilled in the art. The filtrate is then concentrated to the desired concentration level. Furthermore, the berries themselves may then have the juices therefrom extracted and mixed with the extraction. It is contemplated that other alcohols among which are methanol, ethanol and propanol may be employed for the extraction.

In another embodiment of the invention, an ointment of the mountain ash berry extract may be employed. The extract may be obtained from the alcohol solution by any suitable means such as vacuum drying, freeze drying, etc. The extract can then be formulated as an ointment employing such carriers as lactose, starch, various stearates, talc or others. The concentration of extract employed can range from about 1 to about 5 percent by weight.

Although it is not known what the active ingredients are that are effective in suppressing the herpes simples virus, it is known that among other chemicals present in the berries, the following have been identified: hydroxycinnamic acids, anthocyanin, leucoanthocyanin, various flavonals, B-carotene, B-carotene monoepoxide, cryptoxanthin, violaxanthin, gallic acid maringin, meratin, asozane, isoquercetin, and isoquercitrin. It is apparent, however, that the active ingredient or ingredients are obtained by an isopropanol extraction of the mountain ash berries. The extract was obtained in the following manner: a liter quantity of whole mountain ash berries is placed into a four liter container. Two liters of isopropyl alcohol, 70 percent by volume, is added to the berries and allowed to set at room temperature for about four weeks. The liquid is then filtered off from the berries to obtain the extract. The berries are then crushed and the juice therefrom is added to the extract. The filtrate is then concentrated resulting in a concentration of 1 percent by weight of mountain ash berry extract. This concentrate is then employed as shown in the Example.

EXAMPLE

A subject having several lesions of herpes simplex virus about the lips of the mouth had one lesion treated with a 70 percent isopropanol-water solution containing 1 percent of the extract as obtained above. The treatment was repeated four times daily. Another lesion was treated at the same time with a 70 percent isopropanol water solution. The lesion treated with the berry extract was essentially clear within four days. The other lesion was still active after seven days.

The embodiments of the invention in which an exclusive property or privilege is claimed are defined as follows:

1. A method for suppressing herpes simplex virus comprising administering topically to a subject infected with said virus, a composition of an extract of mountain ash berries, a dosage effective for the suppression of said virus.

2. The method of claim 1 wherein said composition comprises from about 0.1 to about 20 percent by weight extract.

3. The method of claim 1 wherein said composition comprises about 1 percent by weight of berry juice.

4. The method of claim 1 wherein said extract is obtaining by extracting mountain ash berries with a solution of isopropyl alcohol.

5. The method of claim 1 wherein said composition comprises a 70 volume percent isopropanol water solution containing 1 percent by weight of berry juice.

6. The method of claim 1 wherein said composition comprises an ointment containing 1 percent by weight of berry juice.

* * * * *